(12) United States Patent
Matsuyama et al.

(10) Patent No.: US 9,644,181 B2
(45) Date of Patent: May 9, 2017

(54) CELL PREPARATION CONTAINING MYOCARDIUM-COMMITTED CELL

(71) Applicants: RIKEN, Wako-shi, Saitama (JP); Akifumi Matsuyama, Wako-shi, Saitama (JP)

(72) Inventors: Akifumi Matsuyama, Saitama (JP); Hanayuki Okura, Hyogo (JP)

(73) Assignees: RIKEN, Saitama (JP); Akifumi Matsuyama, Saitama (JP)

( * ) Notice: Subject to any disclaimer, the term of this patent is extended or adjusted under 35 U.S.C. 154(b) by 105 days.

(21) Appl. No.: 14/396,449

(22) PCT Filed: Apr. 25, 2013

(86) PCT No.: PCT/JP2013/062798
§ 371 (c)(1),
(2) Date: Feb. 18, 2015

(87) PCT Pub. No.: WO2013/162057
PCT Pub. Date: Oct. 31, 2013

(65) Prior Publication Data
US 2015/0291934 A1 Oct. 15, 2015

(30) Foreign Application Priority Data
Apr. 25, 2012 (JP) ................................. 2012-100362

(51) Int. Cl.
*C12N 5/077* (2010.01)
*A61L 27/38* (2006.01)
*A61K 35/34* (2015.01)
*A61K 35/28* (2015.01)
*A61L 27/54* (2006.01)

(52) U.S. Cl.
CPC ............ *C12N 5/0657* (2013.01); *A61K 35/28* (2013.01); *A61K 35/34* (2013.01); *A61L 27/3834* (2013.01); *A61L 27/3873* (2013.01); *A61L 27/3895* (2013.01); *A61L 27/54* (2013.01); *A61L 2300/204* (2013.01); *A61L 2430/20* (2013.01); *A61L 2430/30* (2013.01); *C12N 2500/46* (2013.01); *C12N 2501/999* (2013.01); *C12N 2506/1384* (2013.01)

(58) Field of Classification Search
CPC .......... C12N 5/0657; C12N 2506/1384; C12N 2500/46; A61L 27/3895; A61L 27/3834; A61L 2430/20; A61K 35/28
See application file for complete search history.

(56) References Cited

U.S. PATENT DOCUMENTS

2005/0214939 A1 9/2005 Gold et al.

FOREIGN PATENT DOCUMENTS

| EP | 2166084 A1 | 3/2010 |
|---|---|---|
| EP | 2432482 A1 | 3/2012 |
| JP | 2006-218035 A | 8/2006 |
| JP | 2008-307205 A | 12/2008 |
| WO | WO 2007/108689 A2 | 9/2007 |
| WO | WO 2008/153179 A1 | 12/2008 |

OTHER PUBLICATIONS

English translation of JP2006218035. 2005. p. 1-4.*
Iida et al. Identification of cardiac stem cells with FLK1, CD31, and VE-cadherin expression during embryonic stem cell differentiation. FASEB J. 19, 371-378 (2005).*
Tjabringa et al. The polymine spermine regulates osteogenic differentiation in adipose stem cells. J. Cell. Mol. Med. vol. 12, No. 5A, 2008. p. 1710-1717.*
Supplementary European Search Report dated Dec. 1, 2015, in EP 13782434.8.
Tipnis et al., "Mechanism of Polyamine Toxicity in Cultured Cardiac Myocytes," Toxicology in Vitro, 1998, 12:233-240.

* cited by examiner

*Primary Examiner* — Taeyoon Kim
(74) *Attorney, Agent, or Firm* — Foley & Lardner LLP

(57) ABSTRACT

The present invention relates to a method for producing a cell population comprising myocardium-committed cells that differentiate into and survive as myocardial cells under a myocardial tissue environment. Specifically, the method is characterized in that adipose-tissue-derived multi-lineage/multi-potent progenitor cells are cultured in the presence of a polyamine. The present invention further relates to a cell population comprising the myocardium-committed cells, a cell preparation comprising the cell population, or a cell sheet. The present invention further relates to a method for treating a heart disease, which comprises administering the cell population to a subject.

4 Claims, 12 Drawing Sheets

A

B

C

D

A

B

C

D

E

F

CELL PREPARATION CONTAINING MYOCARDIUM-COMMITTED CELL

CROSS-REFERENCE TO RELATED APPLICATIONS

This application is a National Stage application of PCT/JP2013/062798, filed Apr. 25, 2013, which claims priority from Japanese application JP 2012-100362 filed Apr. 25, 2012.

TECHNICAL FIELD

The present invention relates to a method for producing a cell population comprising myocardium-committed cells, a cell population obtained by the method, and the like.

BACKGROUND ART

Adult myocardial cells have no proliferative capacity. Hence, once damaged myocardium remains unrepaired, patients develop heart failure with a permanent malfunction. As arteriosclerotic vascular diseases increase due to the aging of population and westernized lifestyle habit, the number of heart failure patients is increasing. Particularly in the case of severe heart failure such as ischemic cardiomyopathy, by which remaining cardiac stem cells disappear due to frequent myocardial infarction, medical treatment has not been sufficiently effective. Also, blood flow improved by PCI (coronary angioplasty) and coronary artery bypass surgery has only a limited effect. The annual death rate at the end stage of severe heart failure that is refractory to these treatments is considered to be about 75%. Development of novel therapeutic methods and pharmaceutical products is expected.

Patent Literature 1 discloses a method for preparing myocardial grafts by culturing ES cells during induction of differentiation in the presence of a polyamine such as spermine. Cells after treated with spermine are pace maker-like myocardial cells, into which the differentiation has been induced.

Patent Literature 2 discloses a method for forming a cell sheet containing cardiac myoblast cells, wherein the method comprises: culturing adipose tissue-derived stem cells in the presence of DMSO, or an OP9 culture supernatant, to differentiate into cardiac myoblast cells; and forming a cell sheet containing the cardiac myoblast cells.

PRIOR ART LITERATURE

Patent Literature

Patent Literature 1: JP Patent Publication (Kokai) No. 2006-218035 A
Patent Literature 2: JP Patent Publication (Kokai) No. 2008-307205 A

SUMMARY OF THE INVENTION

An object of the present invention is to produce a cell population comprising (or containing) myocardium-committed cells that differentiate into and survive as myocardial cells under a myocardial tissue environment.

As a result of screening about 4000 types of candidate compounds that induce the differentiation of adipose-tissue-derived multi-lineage/multi-potent progenitor cells (hereinafter, also referred to as "ADMPC") into myocardium-committed cells, in order to achieve the above object, the present inventors have now found that a cell population comprising myocardium-committed cells capable of differentiating into and surviving as myocardial cells under a myocardial tissue environment can be produced by culturing adipose-tissue-derived multi-lineage/multi-potent progenitor cells in the presence of polyamine, thereby completing the present invention. Specifically, the present invention encompasses the following [1] to [23].

[1] A method for producing a cell population comprising myocardium-committed cells, comprising a step of culturing adipose-tissue-derived multi-lineage/multi-potent progenitor cells in the presence of a polyamine.

[2] The method according to [1], comprising a step of culturing the adipose-tissue-derived multi-lineage/multi-potent progenitor cells for 1 to 5 days after the addition of polyamine.

[3] The method according to [1] or [2], wherein the concentration of the polyamine in a medium ranges from 5 μM to 1 mM.

[4] The method according to any one of [1] to [3], wherein the polyamine is a compound represented by the following formula (I):

$$H_2N-X-NH_2 \qquad (I)$$

[wherein X is a $C_{4-14}$ linear hydrocarbon group in which a $CH_2$ group or $CH_2$ groups of the backbone chain may be substituted with 1-4 NH groups].

[5] The method according to any one of [1] to [4], wherein the polyamine is selected from the group consisting of putrescine, spermine, and spermidine.

[6] A cell population comprising myocardium-committed cells, which is obtained by the method of any one of [1] to [5].

[7] A cell preparation comprising the cell population of [6].

[8] A cell preparation for treating a heart disease, comprising the cell population of [6].

[9] A cell sheet comprising the cell population of [6].

[10] A method for producing a cell sheet, comprising the steps of:
producing a cell population comprising myocardium-committed cells by the method of any one of [1] to [5]; and
culturing the cell population to form a cell sheet.

[11] A method for treating a heart disease, comprising: administering the cell population of [6] or the cell preparation of [7] or [8] to a subject; or transplanting the cell sheet of [9] to a damaged heart site of a subject.

[12] The method according to [11], wherein the heart disease is an ischemic heart disease.

[13] The method according to [11] or [12], wherein the cell population is administered at $1 \times 10^4$ to $1 \times 10^9$ cells/kg body weight.

[14] The method according to [1] to [5], wherein the adipose-tissue-derived multi-lineage/multi-potent progenitor cells are autologous cells or allogenic cells.

[15] The cell preparation according to [7], wherein the adipose-tissue-derived multi-lineage/multi-potent progenitor cells are allogenic cells.

[16] The cell preparation for treating a heart disease according to [8], wherein the adipose-tissue-derived multi-lineage/multi-potent progenitor cells are allogenic cells.

[17] The cell preparation according to [15] or [16], which does not comprise an immunosuppressive agent as an ingredient.

[18] The cell sheet according to [9], wherein the adipose-tissue-derived multi-lineage/multi-potent progenitor cells are allogenic cells.

[19] The method according to any one of [11] to [13], wherein the adipose-tissue-derived multi-lineage/multi-potent progenitor cells are allogenic cells.
[20] The method according to [19], comprising no step of immunosuppression.
[21] The method according to [20], wherein the step of immunosuppression is a step of administering an immunosuppressive agent.
[22] A kit comprising the cell preparation of any one of [7], [8] and [15] to [17] and an instruction describing that a step of immunosuppression is not comprised during administration to a subject.
[23] A package comprising the cell preparation of any one of [7], [8] and [15] to [17] and an instruction that a step of immunosuppression is not comprised during administration to a subject.

This description comprises all or part of the contents disclosed in the description and/or drawings of Japanese Patent Application No. 2012-100362, from which the present application has priority.

MODES FOR CARRYING OUT THE INVENTION

Figure 1:
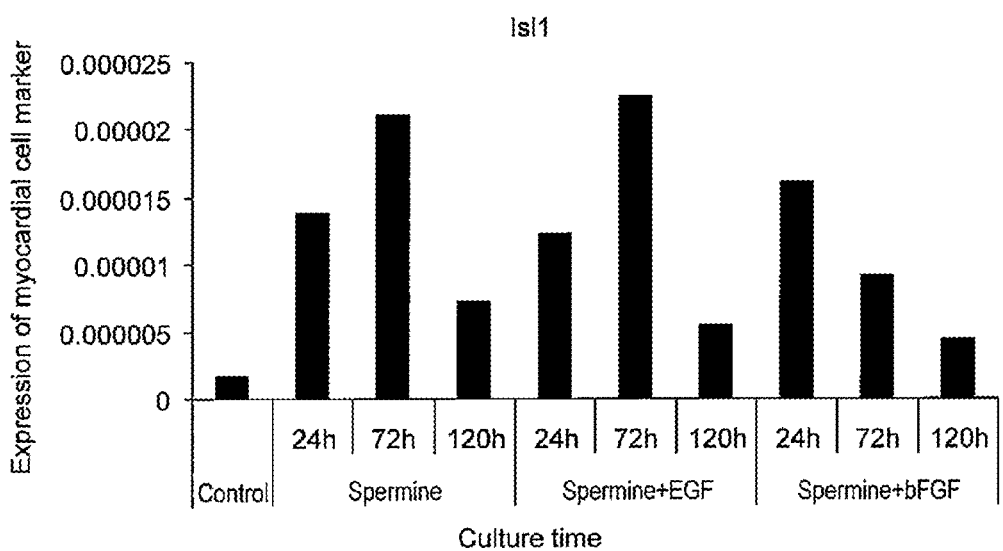
FIG. 1 shows the effects of culture time and growth factors on the expression of various differentiation markers in myocardium-committed cells, which have been produced by induction of differentiation from adipose-tissue-derived multi-lineage/multi-potent progenitor cells in the presence of a polyamine (FIG. 1A-G).
Figure 1:
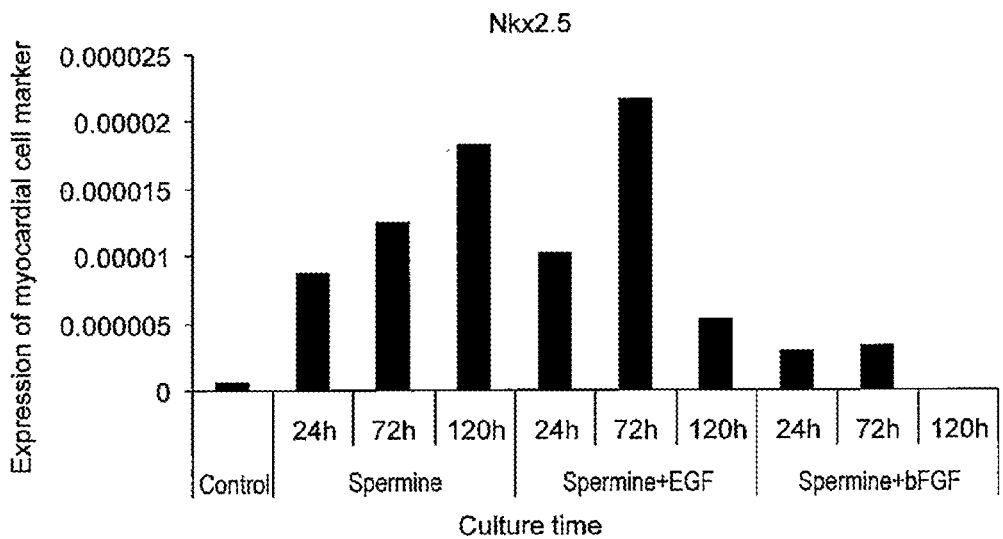
Figure 1:
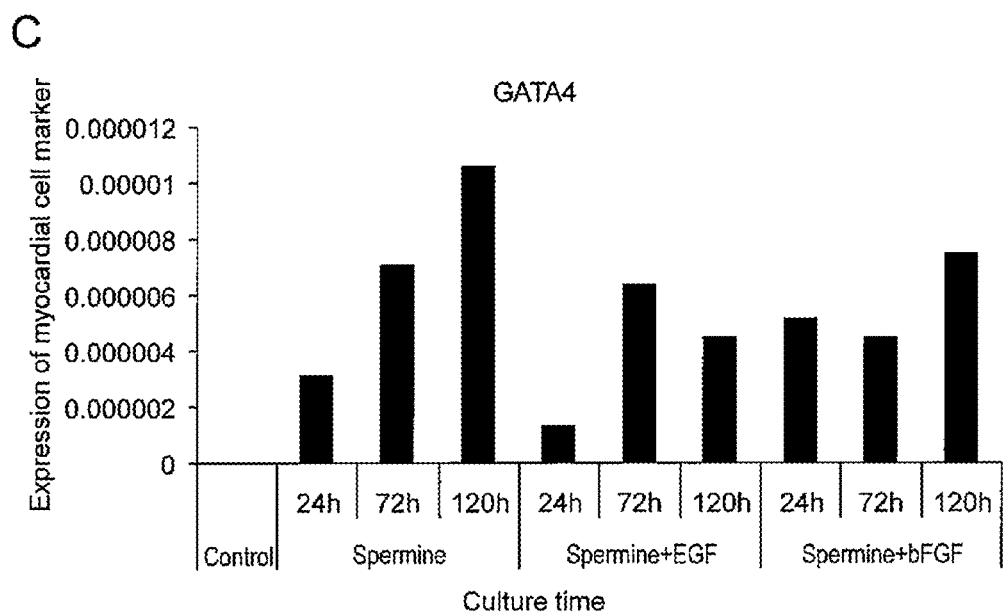
Figure 1:
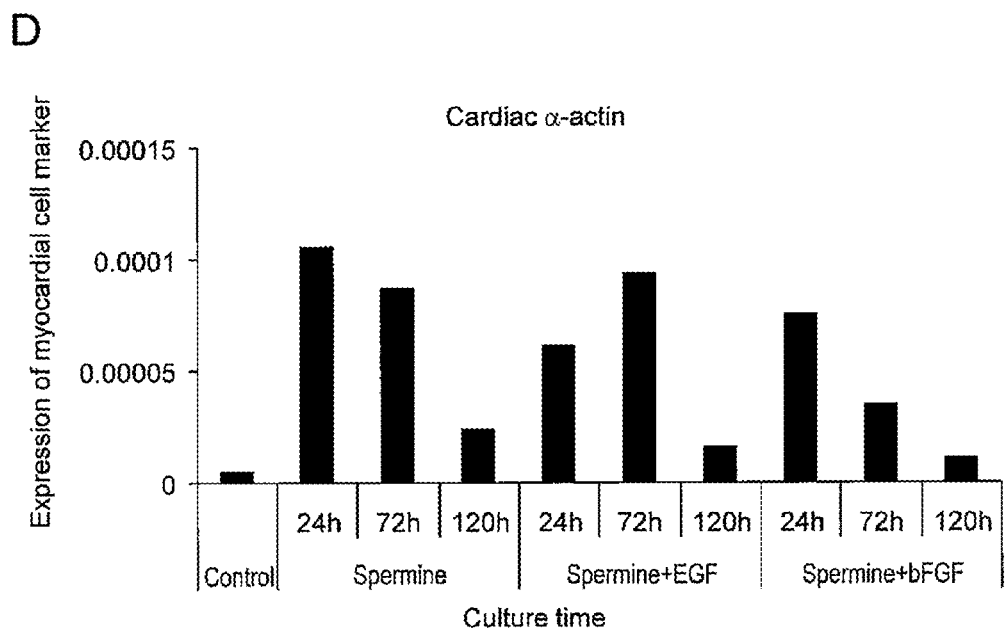
Figure 1:
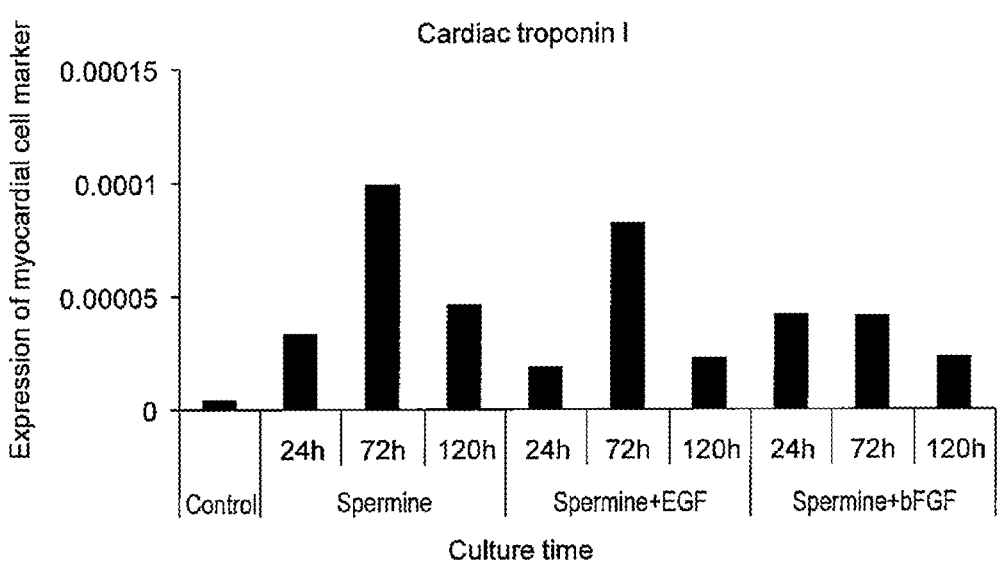
Figure 1:
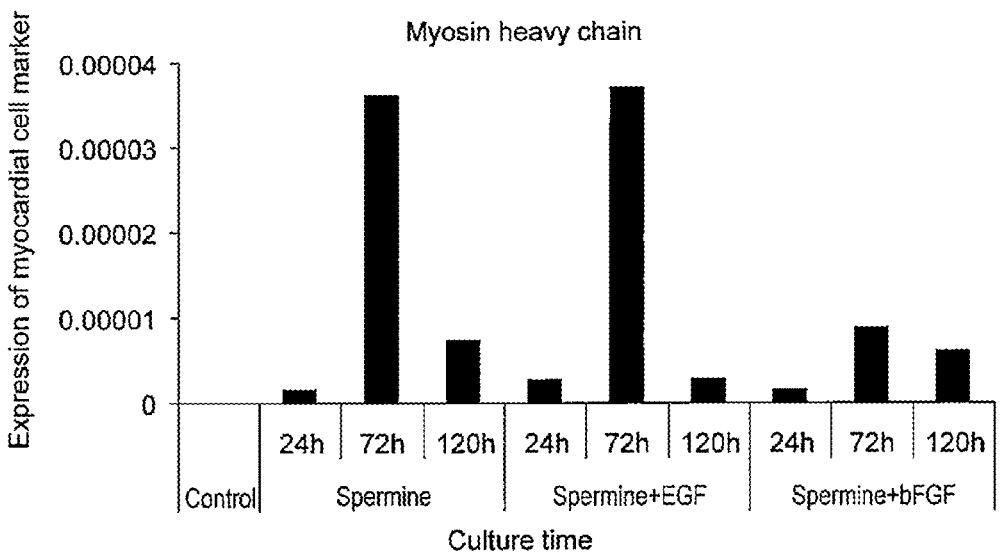
Figure 1:
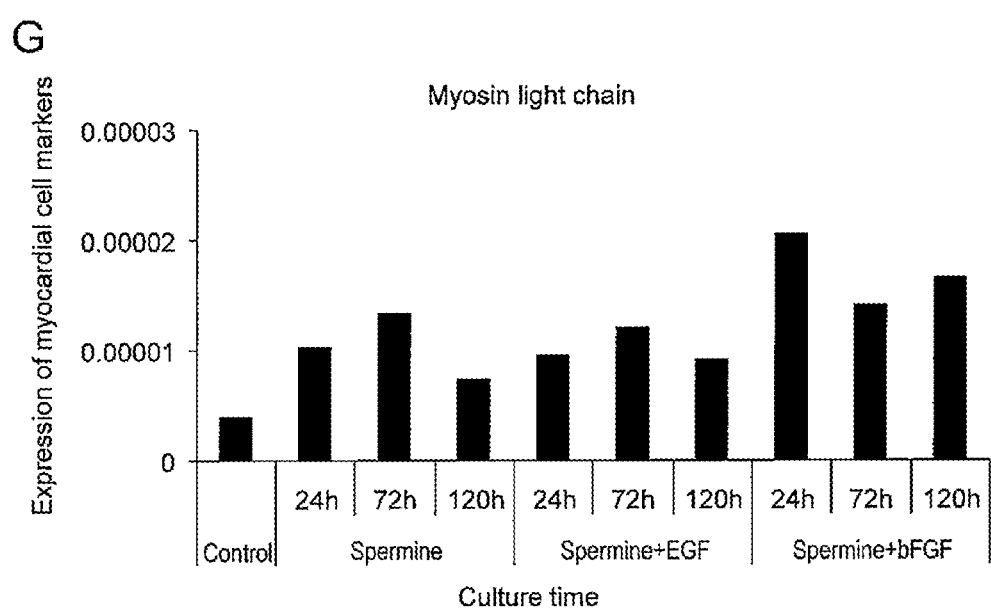
Figure 2:
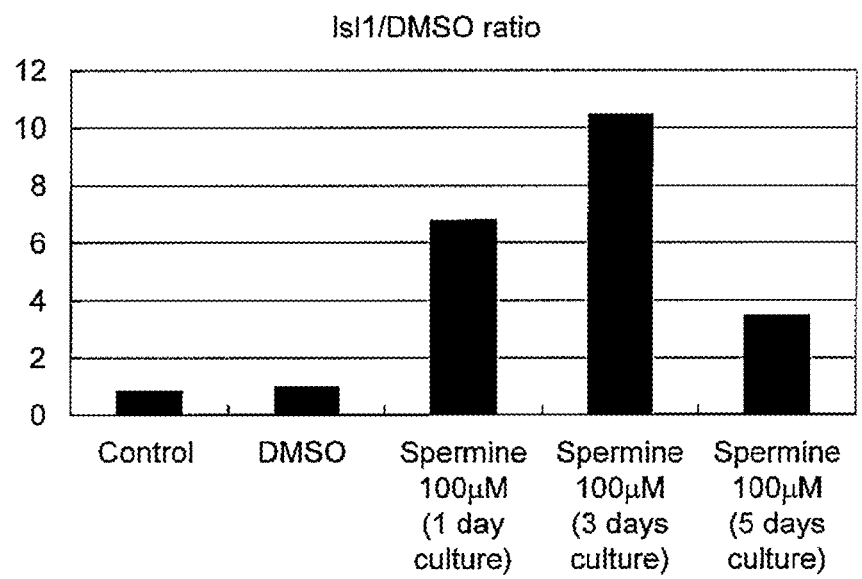
FIG. 2 shows the results of comparing the effects of spermine with the effects of DMSO on the induction of the differentiation of adipose-tissue-derived multi-lineage/multi-potent progenitor cells into myocardium-committed cells (FIG. 2A-G).
Figure 2:
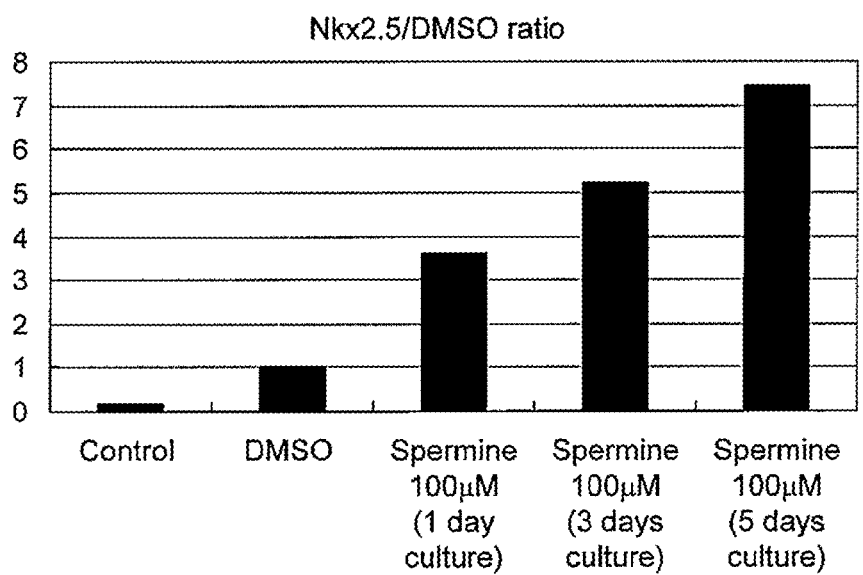
Figure 2:
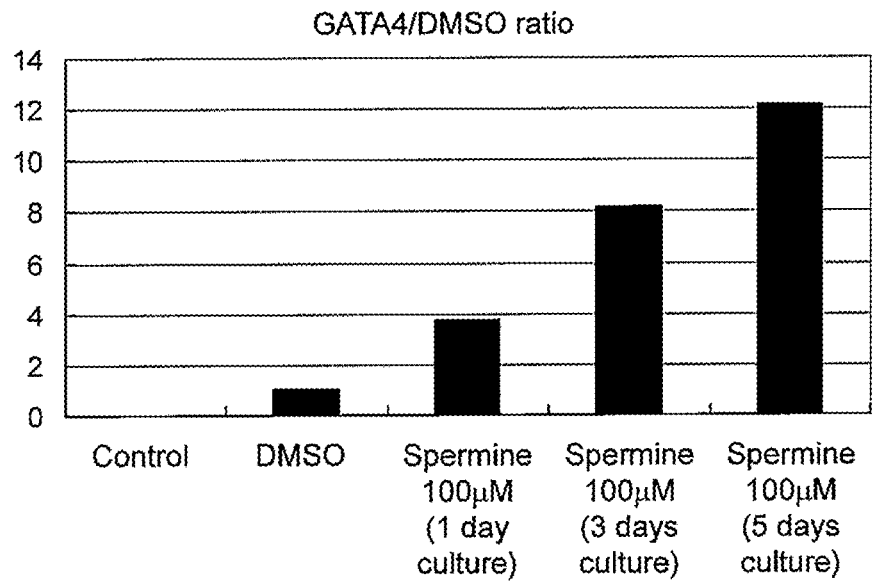
Figure 2:
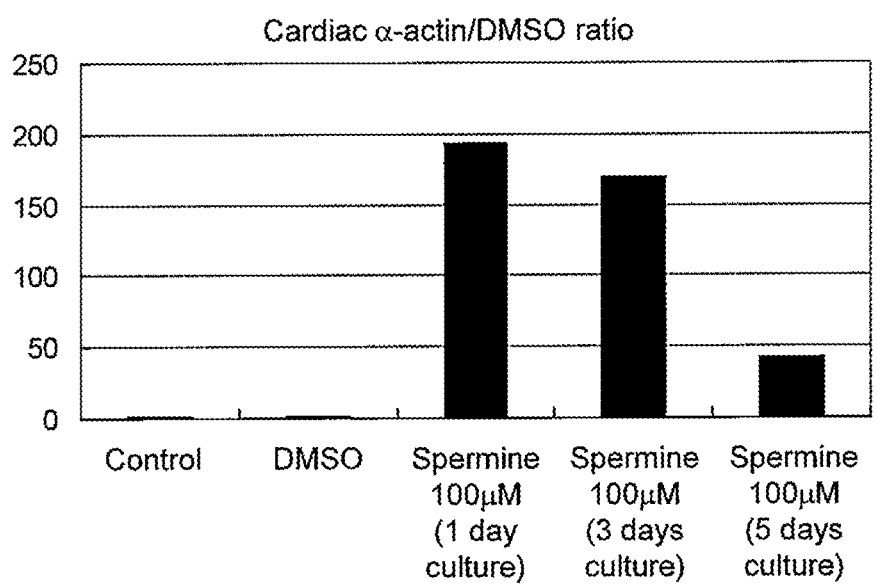
Figure 2:
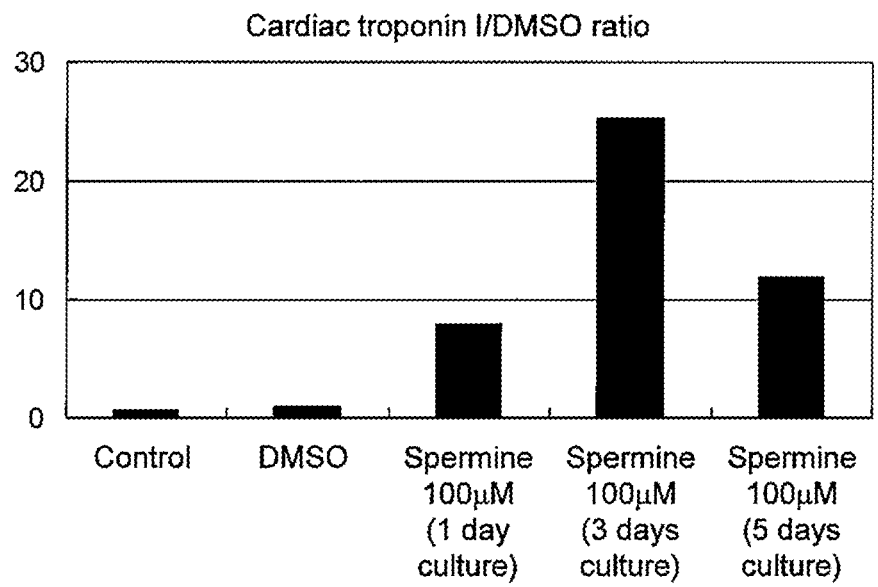
Figure 2:
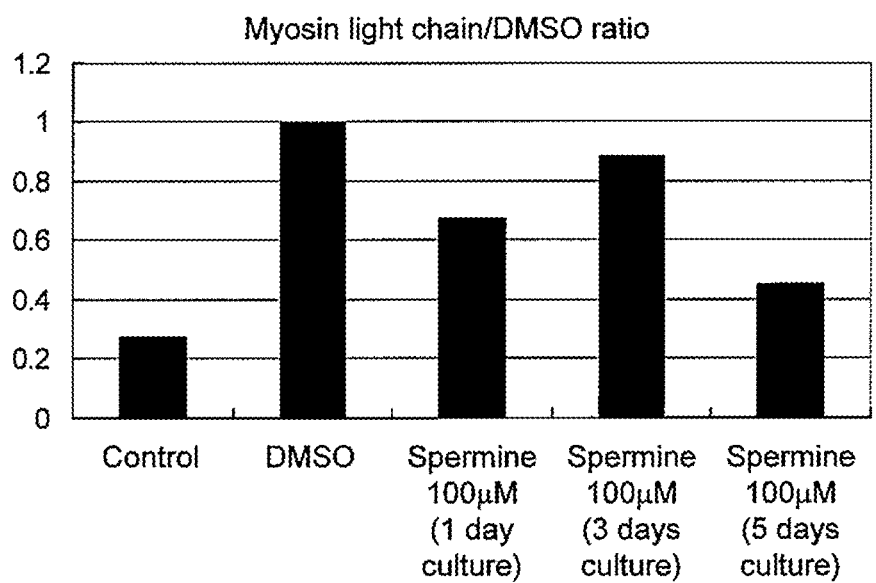
Figure 2:
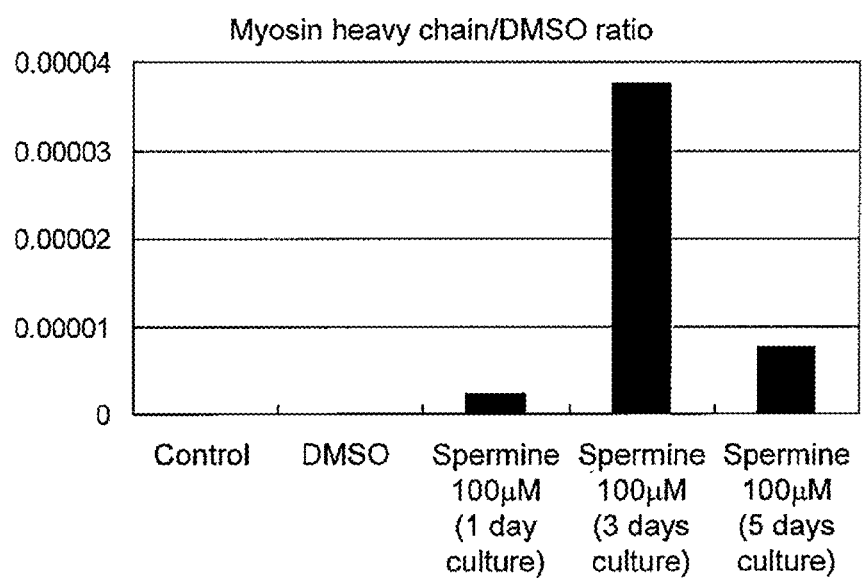

Hereinafter, the present invention will be described in detail.

<Cell Population Comprising Myocardium-Committed Cells>

According to the present invention, the cell population comprising myocardium-committed cells can be produced by culturing adipose-tissue-derived multi-lineage/multi-potent progenitor cells in the presence of a polyamine.

The term "adipose-tissue-derived multi-lineage/multi-potent progenitor cells" as used herein refers to a type of somatic stem cells found by the inventors of the present application and cells capable of differentiating into various cell lineages such as endoderm, mesoderm, and ectoderm. The cells are characterized by expressing an undifferentiation marker, Islet-1, and others, i.e., CD29, CD44, CD73, CD105, and CD166 (WO2008/153179). Animal species from which adipose-tissue-derived multi-lineage/multi-potent progenitor cells are derived include, but are not particularly limited to, humans, mice, rats, rabbits, dogs, cats, cattle, horses, monkeys, and pigs, more preferably humans. When treatment is performed using adipose-tissue-derived multi-lineage/multi-potent progenitor cells, the cells to be used herein are preferably derived from the same species as that of a subject. Cells that are used in the present invention are autologous cells (genetically autogeneic) or allogeneic cells (genetically allogeneic).

The above adipose-tissue-derived multi-lineage/multi-potent progenitor cells can be prepared by the known method described in WO2008/153179, for example. Specifically, adipose tissue is collected from a subject, and then treated with collagenase, and the digested product is filtered. Subsequently, erythrocytes are removed from the thus obtained adipose-tissue-derived cell population. Next, cells other than adipose-tissue-derived multi-lineage/multi-potent progenitor cells are removed from the thus obtained cell population, and thus adipose-tissue-derived multi-lineage/multi-potent progenitor cells can be obtained.

Moreover, a person skilled in the art can prepare cells functionally equivalent to adipose-tissue-derived multi-lineage/multi-potent progenitor cells that are collected from a subject and are cells subjected to the introduction of a gene or the like and/or treatment with a low-molecular-weight compound so that the relevant gene is expressed by any cell by known methods (JP Patent Publication (Kokai) No. 2009-142278 A; Szabo et al., Nature 2010, 468 (7323), 521-6; Ladewig et al., Nat Methods. 2012, April 8) with reference to the gene expression profiles of an undifferentiation marker, Islet-1, and others, i.e., CD29, CD44, CD73, CD105, and CD166. In the present application, cells prepared as described above are also included in the "adipose-tissue-derived multi-lineage/multi-potent progenitor cells.

In the present invention, cells of the cell population comprising adipose-tissue-derived multi-lineage/multi-potent progenitor cells can be used as starting cells for inducing the differentiation into myocardium-committed cells.

The term "polyamine" as used herein refers to a linear aliphatic hydrocarbon, wherein 2 or more primary amino groups are linked, such as 1,3-diaminopropane, putrescine, cadaverine, caldine, spermidine, homospermidine, aminopropylcadaverine, termine, spermine, thermospermine, canavalmine, aminopentyl norspermidine, N,N-bis(aminopropyl)cadaverine, homospermine, caldopentamine, homocaldopentamine, caldohexamine, homocaldohexamine, and diethylenetriamine. A preferable example thereof is a compound represented by the following formula (I):

$$H_2N—X—NH_2 \quad (I)$$

[wherein, X is a $C_{4-14}$ linear hydrocarbon group, in which a $CH_2$ group or $CH_2$ groups of the backbone chain may be substituted with 1-4 NH groups, provided that the number of NH groups to be substituted ranges from 1 to 3 when the number of carbons is 4.].

In the structure of formula (I), $H_2N—NH—$ arrangement and $—NH—NH—$ arrangement are not preferred. More preferably, in the above formula (I), 1 or 2 NH groups are contained when the number of carbons ranges from 4 to 7, 1, 2 or 3 NH groups are contained when the number of carbons ranges from 8 to 12, and 1, 2, 3 or 4 NH groups are contained when the number of carbons ranges from 13 to 14. In the above formula (I), particularly preferably the number of carbons ranges from 8 to 12 and 1, 2 or 3 NH groups are contained. More preferably the polyamine to be used herein is putrescine, spermine or spermidine, and particularly spermine or spermidine is preferred. These polyamines can be used alone or in a form of mixture depending on the purposes and applications of the present invention.

The term "myocardium-committed cells" as used herein refers to cells that have been committed to differentiate into myocardial cells and express at least intranuclear transcription factors, Nkx2.5 and Islet-1. The myocardium-committed cells further preferably express GATA-4, cardiac α-actin (α-CA), cardiac troponin I, myosin light chain (or MLC) and/or myosin heavy chain (or MHC) and have the relative expression profile (of each of these genes) different from that of cardiac myoblasts prepared in the presence of DMSO. Intranuclear transcription factors, Nkx2.5 and Islet-1, are considered to be important in inducing the differentiation of the stem cells into myocardial progenitor cells or myocardial cells. It is known that GATA-4 is located downstream of Nkx2.5 and Islet-1 and that the activation of GATA-4 induces transcription of myocardium-constituting proteins. Moreover, the myocardium-committed cells of the present invention are not completely differentiated pulsating myocardial cells. Animal species from which the myocardium-committed cells are derived include, but are not particularly limited to, mammals such as humans, mice, rats, rabbits, dogs, cats, cattle, horses, monkeys, and pigs, more preferably humans. When treatment is performed using the myocardium-committed cells, the cells are preferably derived from the same species as that of a subject to be treated.

The term "cell population comprising myocardium-committed cells" as used herein refers to a population of cells containing at least the above myocardium-committed cells. These cells may contain the above adipose-tissue-derived multi-lineage/multi-potent progenitor cells, and other cells, which are contaminants, such as erythrocytes, vascular endothelial cells, and fibroblasts. Such a cell population preferably contains myocardium-committed cells in a percentage of at least 10%, 20%, 30%, 40%, 50%, 60%, 70%, 80%, 90%, 95% or 100% in all cells. The percentage of myocardium-committed cells in all cells can be determined using a method known by a person skilled in the art, specifically by quantifying the expression levels of myocardium-committed-cell marker genes, Nkx2.5, as well as Islet-1, GATA-4, α-CA, cardiac troponin I, MLC and/or MHC, for example using quantitative RT-PCR.

The above myocardium-committed cells can be obtained from the above adipose-tissue-derived multi-lineage/multi-potent progenitor cells by, for example, culturing adipose-tissue-derived multi-lineage/multi-potent progenitor cells by means of plate culture, performing medium exchange with a polyamine containing medium, and then culturing for a predetermined time period (at 37° C. and under 5% $CO_2$). Alternatively, the myocardium-committed cells can be obtained by detaching adipose-tissue-derived multi-lineage/multi-potent progenitor cells similarly cultured on culture dishes using a cell detachment agent, washing, suspending at a predetermined concentration in a medium supplemented with polyamine, seeding cells on culture dishes, and then culturing the cells for a predetermined time period. The culture system can be adequately scaled up by adjusting culture dishes or the like according to a desired purpose.

As the medium for culturing the above adipose-tissue-derived multi-lineage/multi-potent progenitor cells in the presence of the above polyamine, a known medium for culturing mammalian cells, such as modified Eagle's medium (MEM), Dulbecco's modified eagle medium (DMEM), William's E medium, Ham's F-10 medium, F-12 medium, PRMI-1640 medium, MCDB201 medium, or a mixture thereof, is used. Preferably, a medium having an osmotic pressure adjusted at low level is used (examples thereof include, but are not limited to, Knockout-DMEM and Knockout-DMEM/F-12 (Life Technologies)). Serum may or may not be added. When serum is added, FBS or the like can be added. In addition, a supplement may be added as an alternative to serum. As a supplement, a Knockout Serum Replacement (KSR (Life Technologies)), Stem Sure (trademark) Serum Replacement (SSR) (Wako Pure Chemical Industries, Ltd.), or the like can be added. In addition to these examples, nonessential amino acids, ascorbic acid, dexamethasone, L-glutamine, 2-mercaptoethanol, antibiotics, EGF (Epidermal Growth Factor), bFGF (basic Fibroblast Growth Factor), activin, G-CSF, and the like can be optionally added, however, the examples thereof are not limited thereto. Culture can be performed based on known methods by suspension culture or adhesion culture.

The concentration of polyamine in a medium for producing the above cell population containing myocardium-committed cells can be appropriately determined using, as indicators, the expression profiles (e.g., Nkx2.5 and Islet-1) observed for myocardium-committed cells, and the gene expression levels of Nkx2.5, Islet-1 and the like that are expressed at high levels in myocardium-committed cells. The myocardium-committed cells can be used in the present invention, when the expression levels of Nkx2.5 and Islet-1 are sufficiently higher than those when the cells are cultured in the absence of a polyamine.

As a gene serving as an indicator for the expression profile of the myocardium-committed cells, Nkx2.5 has an expression level 3 or more times greater, preferably 5 or more times greater, and more preferably 7 or more times greater than that of a case where the cells are cultured in the absence of polyamine, for example. As a gene serving as an indicator for the expression profile of the myocardium-committed cells, Islet-1 has an expression level 2.5 or more times greater, preferably 5 or more times greater, and more preferably 7 or more times greater than that of a case where the cells are cultured in the absence of polyamine. Because, for example, the expression of GATA4 and/or myosin heavy chain, which are genes serving as indicators for the expression profile of the myocardium-committed cells, are not confirmed in the cells that are cultured in the absence of polyamine, regarding the GATA4 and/or myosin heavy chain, only the qualitative confirmation of the expression thereof is required. As genes serving as indicators for the expression profile of the myocardium-committed cells, for example, cardiac α-actin has an expression level 2 or more times greater, preferably 3 or more times greater, and more preferably 5 or more times greater than that of a case where the cells are cultured in the absence of polyamine, and cardiac troponin has an expression level 3 or more times greater, preferably 4 or more times greater, and more preferably 5 or more times greater than that of a case where the cells are cultured in the absence of polyamine. A gene for expression profile selected when it is determined whether a cell is the myocardium-committed cell is preferably one or more genes selected from Islet-1, Nkx2.5, GATA4, cardiac α-actin, cardiac troponin, and myosin heavy chain genes, more preferably one or more genes selected from Islet-1, Nkx2.5, GATA4, and myosin heavy chain genes, still more preferably Nkx2.5.

In a method for producing the above cell population comprising myocardium-committed cells, the concentration of a polyamine to be added into a medium ranges from 25 μM to 500 μM, or 50 μM to 250 μM, preferably 70 μM to 230 μM, more preferably 80 μM to 220 μM, for example. Also, in the case of the compound of the above formula (I), the concentration thereof ranges from 5 μM to 1 mM, 25 μM to 500 μM, or 50 μM to 250 μM, preferably 70 μM to 230 μM, more preferably 80 μM to 220 μM, for example. In the case of spermine, the concentration thereof generally ranges from 50 μM to 250 μM, preferably 70 μM to 150 μM, more preferably 80 μM to 120 μM. In the case of spermidine, the concentration thereof generally ranges from 80 μM to 250 μM, preferably 100 μM to 230 μM, more preferably 150 μM to 220 μM.

To obtain a sufficient number of myocardium-committed cells, after the addition of polyamine, cells are desirably cultured for generally 1 to 5 days, preferably 1 to 4 days, and more preferably 1 to 3 days.

To produce the above cell population comprising myocardium-committed cells, ingredients other than polyamine may also be added to a medium. For example, growth factors such as EGF and bFGF can be added.

The method for producing the cell population comprising myocardium-committed cells of the present invention can comprise a washing step for removing polyamine, after culturing adipose-tissue-derived multi-lineage/multi-potent progenitor cells in the presence of a polyamine and then collecting the cell population. Saline, phosphate-buffered saline, Ringer's solution, or the like can be used for washing.

<Cell Preparation Comprising Myocardium-Committed Cells>

The term "cell preparation comprising a myocardium-committed-cell-comprising cell population" as used herein refers to a preparation comprising at least the above cell population which contains myocardium-committed cells. The myocardium-committed-cell-comprising cell population may be in such a state that each cell is suspended, in such a state that cells are aggregated to form cell mass, or in admixture of the two states. The myocardium-committed-cell-comprising cell population is normally suspended in a pharmacologically acceptable diluent carrier, such as saline or buffer. The cell population can be formulated into a cell preparation by adding proteins such as albumin or the like and additives such as pharmacologically active ingredients, where needed, and then putting the obtained product into a container such as a vial, a bag, or a syringe. The number of cells in the cell population comprising myocardium-committed cells per vial or dose can be adjusted to $1 \times 10^5$ to $1 \times 10^9$ cells, for example. Furthermore, the cell population may be concentrated for use as a cell preparation. The carrier for dilution, the proteins, and the additives may be appropriately selected so as to be suitable for the cell population contained in the cell preparation. The cell preparation can also be prepared by further adding a protective agent such as DMSO and then freezing the resultant.

The above cell preparation can be used for treating heart disease. Examples of heart disease are described in the following section, <Method for treating heart disease by administering myocardium-committed cells>.

<Cell Sheet Comprising Myocardium-Committed-Cell-Comprising Cell Population>

The term "cell sheet comprising myocardium-committed-cell-comprising cell population" as used herein refers to a cell sheet that was prepared in the form of sheet via linking or adhesion of cells, which sheet contains at least the above myocardium-committed cells. The cell sheet may be composed of 1 cell layer or 2 or more cell layers. Examples of constituents other than myocardium-committed cells include adipose-tissue-derived multi-lineage/multi-potent progenitor cells, myocardial cells, scaffold for cells, vascular endothelium, and extracellular matrix. Sheet size and thickness can be appropriately selected depending on various conditions such as the size of a damaged region to which the sheet is applied.

The percentage of myocardium-committed cells contained in a sheet is, but is not particularly limited to, for example 5%, 10%, 20%, 30%, 40%, 50%, 60%, 70%, 80%, 90%, 95%, or 100%. The percentage of myocardium-committed cells can be determined by a method known by a person skilled in the art, for example, by quantifying myocardium-committed cell marker genes, Nkx2.5, as well as Islet-1, GATA-4, α-CA, cardiac troponin I, MLC and/or MHC, for example using quantitative RT-PCR.

The functions of the cell sheet of the present invention can be evaluated by a known method, for example, by transplanting the sheet to a subject, and then evaluating the cardiac functions of the subject who received the transplantation by echocardiography or by measuring left ventricular end-diastolic diameter (LVDd), left ventricular end-systolic diameter (LVDs), left ventricular ejection fraction (% EF) or the fractional shortening of left ventricular internal dimension (% FS), for example.

The method for producing the cell sheet of the present invention comprises the steps of: (1) producing a cell population comprising myocardium-committed cells by the above method; and (2) culturing the cell population so as to form a cell sheet. For example, the cell sheet can be obtained by culturing adipose-tissue-derived multi-lineage/multi-potent progenitor cells by means of plate culture, performing medium exchange with a medium comprising polyamine, and then detaching the cell layer after a predetermined time period. Alternatively, the cell sheet is produced by proliferating a myocardium-committed-cell-comprising cell population adhered to culture dishes, so as to cause the cells to form a cell layer, optionally seeding the cell population on the cell layer and similarly culturing the cells to form a new cell layer, optionally repeating the above procedures, and then detaching the thus formed cell layers. The number of myocardium-committed cells to be used herein and the time for culturing these cells can be adequately selected depending on various conditions such as sheet sizes to be obtained, and the number of myocardium-committed cells to be contained in the sheet. Specifically, the myocardium-committed-cell-comprising cell population is cultured in an amount of $1 \times 10^5$ to $5 \times 10^7$ cells per 35-mm culture dish for 24 to 120 hours, so that a cell sheet can be obtained. When the cells are cultured, the number of cells can be adjusted with the area ratio relative to the size of a culture dish. As a culture dish, a 100-mm culture dish can also be used, for example. A cell layer can be detached by, preferably culturing the cells using a temperature-sensitive culture dish and incubating at 20° C. or lower, for example.

<Method for Treating Heart Disease by Administering Myocardium-Committed Cells>

According to the present invention, heart disease can be treated by administering the myocardium-committed-cell-comprising cell population or the cell preparation to a subject. Alternatively, heart disease can be treated by transplanting the above cell sheet to a damaged heart site of a subject.

The term "subject" as used herein refers to a subject to be treated by the method of the present invention. Examples thereof include mammals such as humans, mice, rats, rabbits, dogs, cats, cattle, horses, monkeys, and pigs, preferably humans.

The term "heart disease" as used herein refers to a disease of the heart, such as ischemic heart diseases (e.g., myocardial infarction and angina pectoris) and a terminal symptom thereof, ischemic cardiomyopathy, and heart failure (e.g., dilated cardiomyopathy). Moreover, the method for treating a heart disease of the present invention can be used for treating myocardium after the surgery for congenital heart disease or can be used as a maneuver to be used in combination with operation for making left ventricular.

Methods for administration are not limited, as long as these methods enable the cell preparation of the present invention to reach the heart. Examples thereof include intravenous administration, intraarterial administration, and intramyocardial administration. Specifically, injection into a patient's disease site via an injection needle enables to directly deliver the cell preparation to the site. Moreover, the cell preparation can also be administered via a catheter into the coronary artery. In this case, it is considered that cells are delivered to blood vessels of the heart leading to the coronary artery and infiltrate into the myocardium from the blood vessels so as to be delivered to the myocardium, and are then differentiated and survive.

The number of cell populations to be administered per administration is not particularly limited, as long as it is sufficient for myocardium-committed cells to differentiate into and survive as myocardial cells. For example, the number thereof ranges from $1 \times 10^4$ to $1 \times 10^9$/kg body weight, preferably $1 \times 10^5$ to $1 \times 10^7$/kg body weight, more preferably $1 \times 10^5$ to $1 \times 10^6$/kg body weight. Moreover, the concentration of cells in a cell preparation generally ranges from $1 \times 10^4$ to $1 \times 10^7$ cells/mL, preferably $1 \times 10^5$ to $5 \times 10^6$ cells/mL, more preferably $3 \times 10^5$ to $3 \times 10^6$ cells/mL. Administration may be performed multiple times depending on the conditions of a subject, the severity of a disease, and the like.

When the cell sheet of the present invention is transplanted, for example, the cell sheet can be directly applied to an ischemic site of myocardial tissue damaged due to myocardial infarction, angina pectoris, or the like, or suture, insertion, or the like can be performed after application thereof.

Regarding the cell population of the present invention, adipose-tissue-derived multi-lineage/multi-potent progenitor cells can be prepared from autologous cells or allogenic cells. However, as described later in Example 7, a cell population prepared with allogenic cells or a cell preparation comprising the cell population exhibit, in the subject, an effect of improving cardiac functions to an extent equivalent to or higher than that exhibited by those prepared from autologous cells, without causing any adverse reaction such as rejection, even when no immunosuppressive agent is administered. When the cell population or the cell preparation of the present invention is prepared from the above allogenic cells, the cell population or the cell preparation can be produced independent of cells derived from a patient to which the cell population or the cell preparation is administered. Hence, the cell population or the cell preparation of the present invention is advantageous in terms of production and storage.

Accordingly, the therapeutic method of the present invention can require no step of immunosuppressing a subject. Such a step of immunosuppression generally involves the administration of an immunosuppressive agent. Administration of an immunosuppressive agent is not essential for the therapeutic method of the present invention, and an immunosuppressive agent is used only when needed.

<Kit or Package>

The present invention further provides an instruction describing that administration to a subject involves no step of immunosuppression, and a kit or a package comprising the above cell preparation.

Both the kit and the package are used for treating a heart disease. Preparing the cell preparation of the present invention in such a form makes it possible for health care workers to handle the cell preparation safely and conveniently. The cell preparation is produced by putting the above-mentioned therapeutically effective dose of the cell population into a sterilized container such as a syringe, a vial, or a bag, in places with proper sanitation, as described above.

The instruction includes an additional instruction of excluding the step of immunosuppression upon administration to a subject, in addition to handling of the cell preparation, cautions, and the like.

EXAMPLES

The present invention will be further described in detail by examples as follows, but the scope of the present invention is not limited by these examples.

[Test Method]

<Preparation of Adipose-Tissue-Derived Multi-Lineage/Multi-Potent Progenitor Cells: ADMPC>

Adipose tissues were provided by subjects from whom informed consent had been obtained by suction surgery from subcutaneous tissues. Neither steroid agent nor TZD had been administered to any of the subjects. Adipose tissues were cut into small pieces. Next, digestion was performed for 1 hour with shaking in 0.067% collagenase (Roche applied science)-containing Hanks' Balanced Salt Solution (HBSS) in a water bath at 37° C. The digested products were filtered through a Cell Strainer (BD Bioscience) and then centrifuged at 800 g for 10 minutes. Erythrocytes were removed by a specific gravity method using Lymphoprep (d=1.077) (Nycomed). The thus obtained Stromal Vascular Fraction (cells) was seeded into DMEM containing 10% fetal calf serum (Life Technologies). Cells were cultured for 24 hours so that they would adhere. After washing, the resultant was treated with EDTA, and ADMPC were thereby obtained. Next, ADMPC were seeded on a human-fibronectin-coated dish in medium I: 60% DMEM-low glucose, 40% MCDB201, 10 μg/mL EGF, 1 nM dexamethasone, 100 μM ascorbic acid, and 5% FBS at a density of 10,000 cells/cm², passaged 3 to 5 times, and then used for experiments.

<Expression Analysis of Various Markers by Real-Time PCR>

Total RNA was isolated from the thus obtained cells using an RNeasy mini kit (Qiagen) according to protocols recommended by the manufacturer. Total RNA (500 ng) was subjected to DNase treatment, and then cDNA was synthesized using Superscript III reverse transcriptase RNase H (-) (Life Technologies).

Subsequently, TaqMan Universal PCR Master Mix (Applied Biosystems) (10 μl) and TaqMan Gene Expression Assays (Applied Biosystems) (1 μl) were added to the thus prepared cDNA (9 μl). Real-time PCR was performed using an Applied Biosystems 7900 Fast Real-Time PCR system under the following conditions: denaturation at 95° C. for 10 minutes and 40 cycles of 95° C. for 15 seconds and 60° C. for 1 minute. TaqMan probes and assay IDs (available from GenBank/NCBI (U.S.A.)) used for Islet-1, Nkx2.5, GATA-4, α-CA, cardiac troponin I, MLC, MHC, and GAPDH are listed in Table 1 below.

TABLE 1

| Gene name | Reference sequence | Assay ID |
| --- | --- | --- |
| Islet-1 | NM_002202.2 | Hs00158126_m1 |
| Nkx2.5 | NM_004387.2 | Hs00231763_m1 |
| GATA-4 | NM_002052.3 | Hs00171403_m1 |
| α-CA | NM_005159.4 | Hs01109515_m1 |
| Cardiac troponin I | NM_000363.4 | Hs00165957_m1 |
| MHC | NM_002471.2 | Hs00411908_m1 |
| MLC | NM_000432.3 | Hs00166405_m1 |
| GAPDH | NM_002046.3 | Hs99999905_m1 |

<Analysis of Myocardial Tissue after Cell Transplantation>

12 weeks after administration of the cell preparation of the present invention, pigs were sacrificed, and then the hearts were excised. Each excised heart was fixed with a 4% paraformaldehyde solution, followed by substitution with 70% ethanol. The fixed heart was cut into pieces having a width of several millimeters, and then such pieces were fixed with paraffin, thereby preparing a block. The thus obtained paraffin block was sliced thinly using a microtome to 2 μm. The sections were attached to slide glass and then dried. The thus obtained thin sections were subjected to immunohistochemical staining as described below.

Example 1

Analysis of the Induction of the Expression of Myocardium-Committed-Cell Markers by Spermine To examine the induction of differentiation from ADMPC into myocardium-committed cells by spermine, the expression levels of myocardium-committed intranuclear transcription factors (Islet-1 (also referred to as isl-1 or isl1), nkx 2.5, GATA-4) and myocardial constituting proteins (α-CA, cardiac troponin I, myosin heavy chain, and myosin light chain) in the cell population treated with spermine were measured.

ADMPC passaged 4 times by plate culture were detached and washed with TrypLE Select (Life Technologies; the same applies hereafter) and were suspended at a concentration of 1×10$^5$/mL in Knockout-DMEM (Life Technologies; the same applies hereafter) supplemented with 0, 5, 25, 50, 100, 200, or 500 μM or 1 mM spermine (Wako Pure Chemical Industries, Ltd. (Japan); the same applies hereafter) and 20% KSR (Knockout Serum Replacement; Life Technologies; the same applies hereafter). 10 mL of cells was seeded on an EZ-Sphere low-adhesion culture dish (diameter: 10 cm, AGC; the same applies hereafter), and then suspension culture was performed. After 24 hours, cells were collected, quantitative analysis of expression was performed by TaqMan PCR, and then GAPDH ratios were calculated.

As a result, expression was confirmed for all of isl-1, nkx2.5, GATA-4 and α-CA, cardiac troponin I, and MHC. In particular, when 100 μM spermine was added, all markers exhibited the highest expression levels. These results demonstrated that ADMPC are induced by spermine to differentiate into myocardium-committed cells.

Example 2

Analysis of the Induction of the Expression of Myocardium-Committed Cell Markers by Spermidine An experiment was conducted in a manner similar to that of Example 1, except that spermidine (Wako Pure Chemical Industries, Ltd. (Japan)) was added instead of spermine at 0, 5, 25, 50, 100, 200, 500 μM or 1 mM, and the expression levels of myocardium-committed intranuclear transcription factors (isl1, nkx2.5, GATA-4) were analyzed.

As a result, expression was confirmed for all of isl-1, nkx2.5, and GATA-4. In particular, when 200 μM spermidine was added, all markers exhibited the highest expression levels. These results demonstrate that ADMPC are induced by spermidine to differentiate into myocardium-committed cells.

Example 3

Effects of Culture Time Dependency and Growth Factors on the Expression Levels of Various Markers The effects of the time for suspension culture and growth factors (EGF (PeproTech) and bFGF (PeproTech)) on the induction of the differentiation of ADMPC into myocardium-committed cells by 100 μM Spermine were examined.

Induction of the differentiation into myocardium-committed cells was examined as follows. The ratios of the expression levels of myocardium-committed intranuclear transcription factors (isl-1, nkx2.5, and GATA-4) and myocardial constituting proteins (α-CA, cardiac troponin I, MHC, and MLC) to the expression level of GAPDH were examined using ADMPC (before the start of suspension culture) as a control. However, the results for GATA-4 and MHC were represented by GAPDH ratios, since the expression of GATA-4 and MHC was not observed for the control.

In a manner similar to that in Example 1, cells were seeded in culture dishes, collected 24, 72, and 120 hours later, and then subjected to quantitative expression analysis by TaqMan PCR.

Results are shown in FIG. 1. Expression was confirmed for all of isl-1, nkx2.5, and GATA-4, and α-CA, cardiac troponin I, MHC, and MLC at 24 hours to 120 hours later, suggesting the induction of differentiation into myocardium-committed cells. Moreover, the presence or the absence of growth factors did not significantly affect the expression levels.

Example 4

Test for Comparing the Induction of the Expression of Various Markers by Spermine and DMSO In a manner similar to that in Example 1, treatment with DMSO (NACALAI TESQUE, INC. (Japan)) (added at 0.1% in medium) was performed for 48 hours, and, treatment with 100 μM spermine was performed for 24, 72, and 120 hours, and thus the expression levels of various markers were analyzed.

Results are shown in Tables 2 to 8 and FIG. 2A to G. All markers were confirmed to exhibit expression levels enhanced several to several hundred times greater in the case of treatment with spermine than in the case of treatment with DMSO. These results demonstrated that the use of spermine induced the differentiation into myocardium-committed cells to a degree higher than that in the case using DMSO.

TABLE 2

| Isl1/DMSO ratio | |
|---|---|
| Control | 0.87 |
| DMSO | 1 |
| Spermine 100 μM (1 day culture) | 6.79 |
| Spermine 100 μM (3 days culture) | 10.44 |
| Spermine 100 μM (5 days culture) | 3.49 |

TABLE 3

| Nkx2.5/DMSO ratio | |
|---|---|
| Control | 0.18 |
| DMSO | 1 |
| Spermine 100 μM (1 day culture) | 3.58 |
| Spermine 100 μM (3 days culture) | 5.19 |
| Spermine 100 μM (5 days culture) | 7.47 |

TABLE 4

| GATA4/DMSO ratio | |
|---|---|
| Control | Not detected |
| DMSO | 1 |
| Spermine 100 μM (1 day culture) | 3.75 |
| Spermine 100 μM (3 days culture) | 8.19 |
| Spermine 100 μM (5 days culture) | 12.15 |

TABLE 5

| Cardiac α-actin/DMSO ratio | |
|---|---|
| Control | 0.74 |
| DMSO | 1 |
| Spermine 100 μM (1 day culture) | 192.84 |
| Spermine 100 μM (3 days culture) | 169.75 |
| Spermine 100 μM (5 days culture) | 42.85 |

TABLE 6

| Cardiac troponin I/DMSO ratio | |
|---|---|
| Control | 0.64 |
| DMSO | 1 |
| Spermine 100 μM (1 day culture) | 7.91 |
| Spermine 100 μM (3 days culture) | 25.16 |
| Spermine 100 μM (5 days culture) | 11.87 |

TABLE 7

| MLC/DMSO ratio | |
|---|---|
| Control | 0.27 |
| DMSO | 1 |
| Spermine 100 μM (1 day culture) | 0.67 |
| Spermine 100 μM (3 days culture) | 0.88 |
| Spermine 100 μM (5 days culture) | 0.45 |

TABLE 8

| MHC/DMSO ratio | |
|---|---|
| Control | Not detected |
| DMSO | Not detected |
| Spermine 100 μM (1 day culture) | $2.31 \times 10^{-6}$ |
| Spermine 100 μM (3 days culture) | $3.74 \times 10^{-5}$ |
| Spermine 100 μM (5 days culture) | $7.67 \times 10^{-6}$ |

Example 5

Analysis of Myocardial Tissue after Administration of Cell Preparation

A severe myocardial infarction model was prepared by 2-stage embolization•reflux methods using 8-week-old pigs. Specifically, a 6F guide catheter was placed in a percutaneous transluminal manner from the femoral artery to the entrance of the left coronary artery, from which a guide wire was inserted into the first diagonal branch (AHA classification #9). Preconditioning was performed by ballooning (reopening of the occlusion) under the guide. After 1 week, a guide wire was inserted into the anterior descending branch of the left coronary artery (AHA classification #6 to #8). Ballooning (reopening of the occlusion) was performed at the left anterior descending branch (AHA classification #6) immediately below the LCX (left circumflex coronary artery) bifurcation, thereby obtaining myocardial ischemic area. After 4 weeks (5 weeks after the first reopening of the occlusion), individual pigs with cardiac ejection fraction of 35% or less as measured by cardiac ultrasonography examination were subjected to the test as severe heart failure model animals.

4 weeks after the $2^{nd}$ embolization•reflux, cells treated with 100 μM spermine (cultured for 24 hours) were administered at $1 \times 10^5$ cells/kg body weight, $3 \times 10^5$ cells/kg body weight, $1 \times 10^6$ cells/kg body weight, $3 \times 10^6$ cells/kg body weight using a catheter and through the coronary artery. Left ventricular ejection fraction (% EF) was measured by cardiac ultrasonography (echo) immediately before administration, and 1 month, 2 months, and 3 months after administration (FIG. 3A), and examined for a difference ΔEF (%) compared with the value immediately before administration (FIG. 3B). In addition, for the purpose of immunosuppression, intramuscular injection of cyclosporine was performed every day from 5 days before administration of cells to the sacrifice of the test animals.

Figure 3:
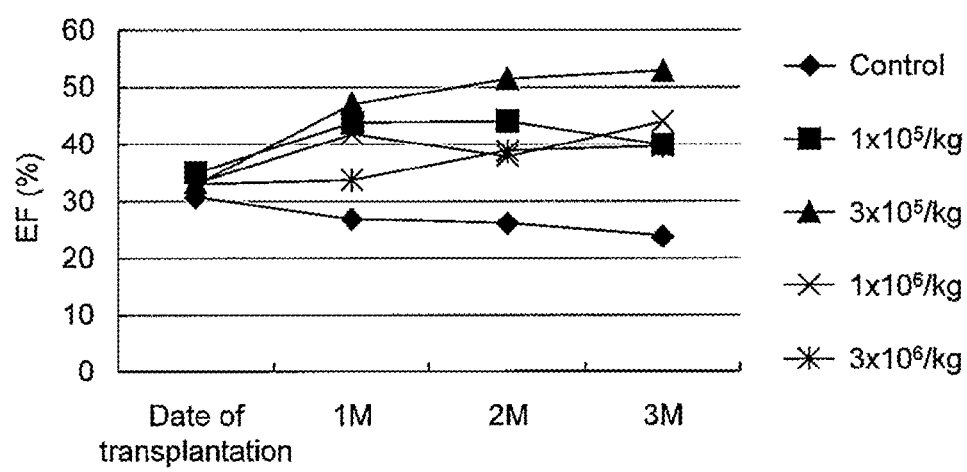
FIG. 3 shows left ventricular ejection fractions (% EF) after administration of the cell preparation of the present invention through the coronary artery to severe myocardial infarction model animals (pigs) (FIG. 3A), and differences ΔEF (%) between these fractions and the fraction immediately before administration (FIG. 3B), wherein the % EF and ΔEF (%) values were examined over time.
Figure 3:
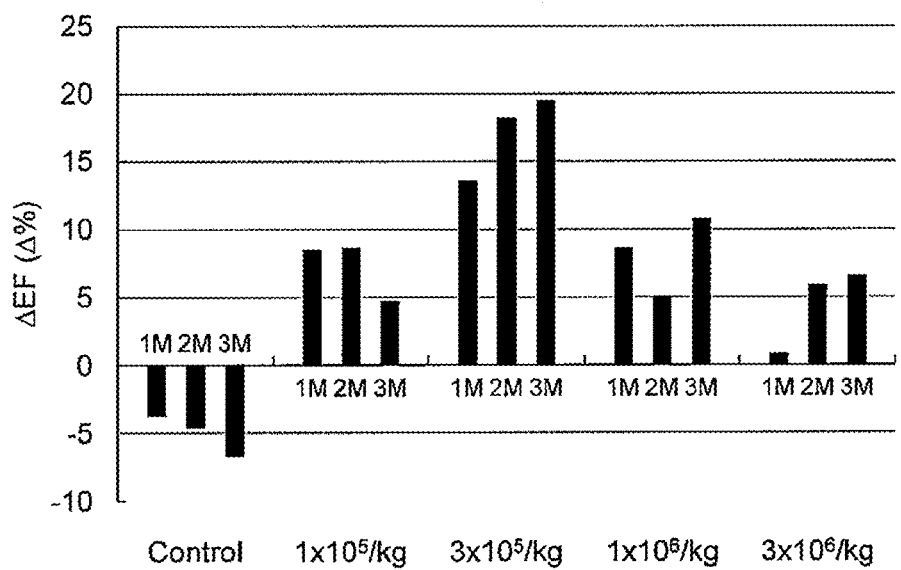

As shown in FIG. 3, while the left ventricular ejection fraction was found to decrease over time for the control, left ventricular ejection fractions were found to be improved in all cases where cells treated with spermine had been administered.

Figure 4:
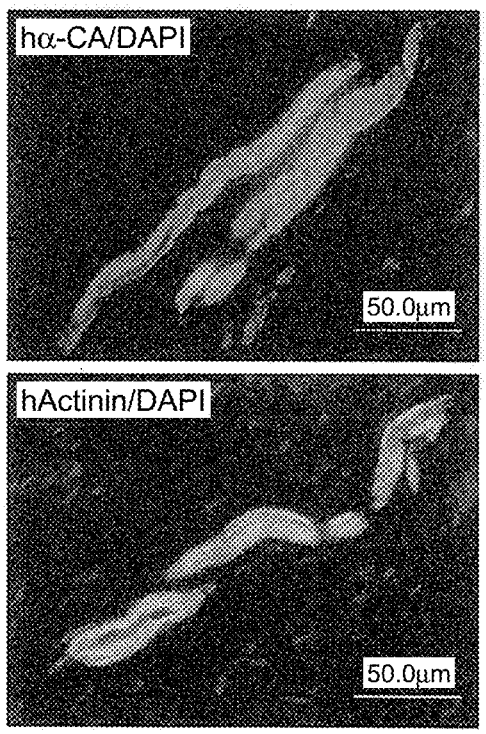
FIG. 4 shows the immunostaining of myocardial tissue sections from the pigs on 12 week after administration of the cell preparation of the present invention, with human-derived α-CA antibody (upper panel) or human-derived actinin antibody (lower panel).

Moreover, FIG. 4 shows the fluorescence images of myocardial tissue sections at 12 weeks after administration immunostained with human-derived α-CA antibody (upper panel) and actinin antibody (lower panel). These results revealed that cells differentiated into and survived as myocardial cells even within the scar after infarction.

Moreover, these administration experiments were carried out similarly for cells treated with DMSO described in Example 4. As a result, cells treated with spermine exhibited significantly higher reproducibility in terms of the percentage of myocardial cells that had survived after differentiation, compared with cells treated with DMSO.

Example 6

Analysis after Repeated Administration of Cell Preparation

Figure 5:
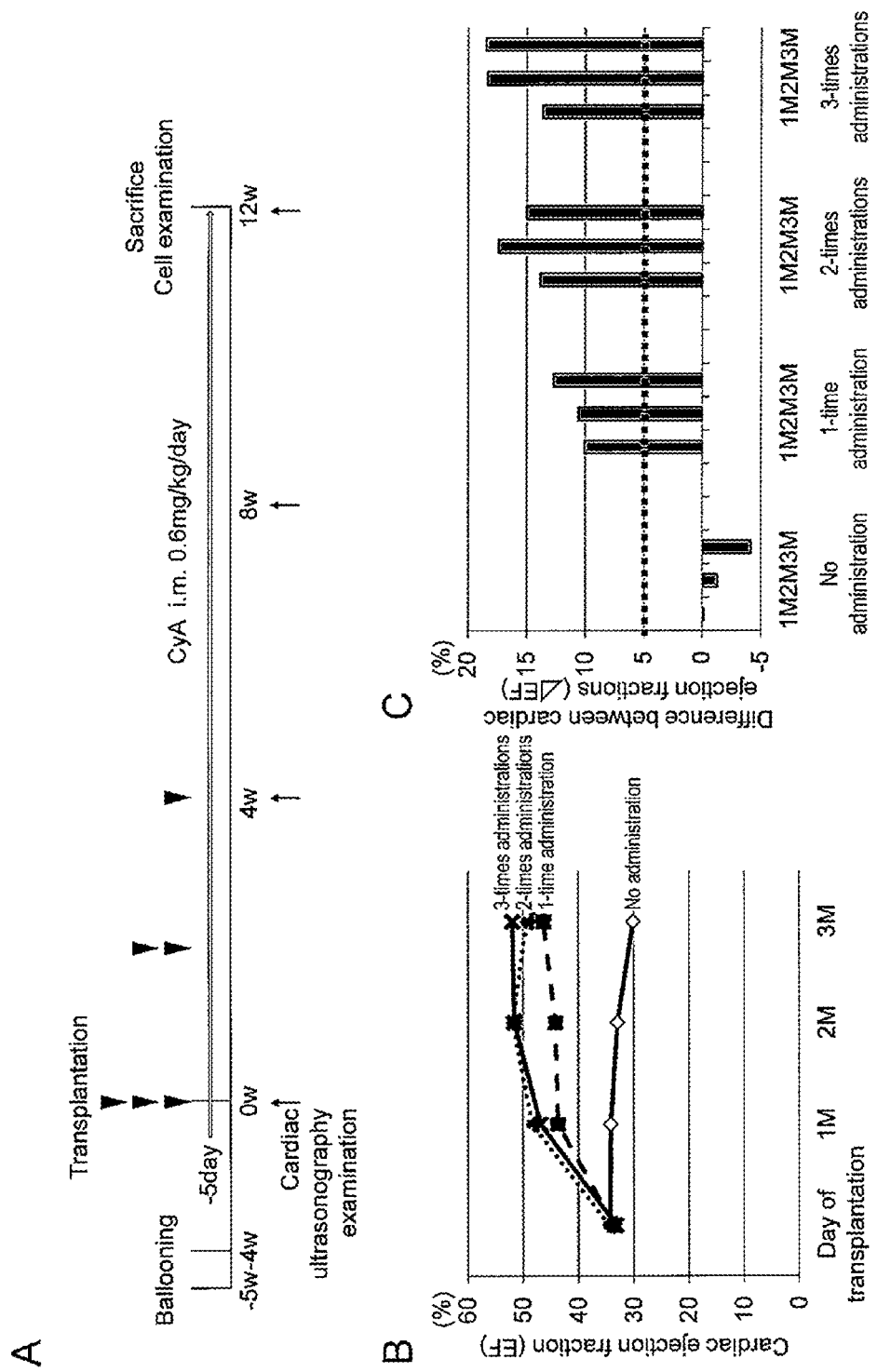
FIG. 5 shows left ventricular ejection fractions (% EF) (FIG. 5B) after repeated administration of the cell preparation of the present invention through the coronary artery to severe myocardial infarction model animals (pigs) according to the schedule shown in FIG. 5A, and differences ΔEF (%) (FIG. 5C) between these fractions and the fraction immediately before administration, wherein the % EF and ΔEF (%) values were examined over time.

The effect of repeated administration on pigs with chronic myocardial infarction serving as severe heart failure model animals prepared in a manner similar to Example 5 was examined. Administration through the coronary artery was performed again 2 weeks later for pigs with chronic myocardial infarction (2-times administrations). Furthermore, administration through the coronary artery was performed 2 weeks and 4 weeks after the initial administration (3-times administrations). Cardiac ejection fraction (EF) was calculated 1 month, 2 months, and 3 months after the initial administration in a manner similar to that in Example 5 (FIG. 5).

As a result of a test for the effective accumulation due to the above repeated administration, differences (ΔEF) in cardiac ejection fraction were 10% and 5% or higher, confirming the effective accumulation due to multiple administrations.

Example 7

Figure 6:
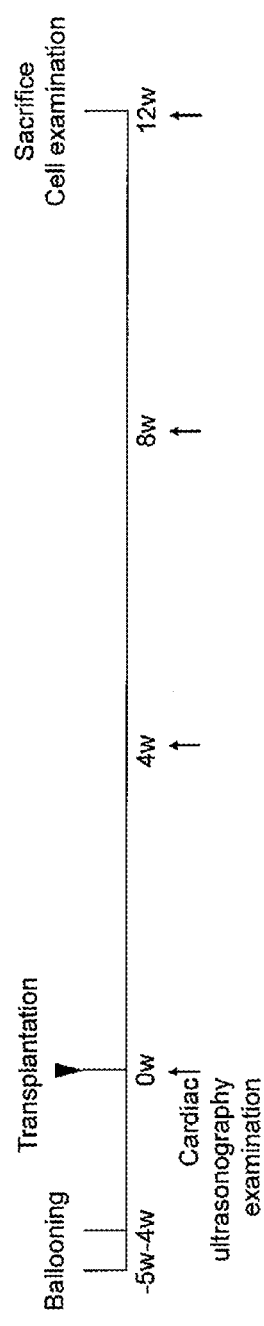
FIG. 6 shows left ventricular ejection fractions (% EF) (FIG. 6B) after administration of the cell preparation of the present invention prepared with autologous cells or allogenic cells through the coronary artery to severe myocardial infarction model animals (pigs) according to the schedule shown in FIG. 6A, and differences ΔEF (%) (FIG. 6C) between these fractions and the fraction immediately before administration, wherein the % EF and ΔEF (%) values were examined over time.
Figure 6:
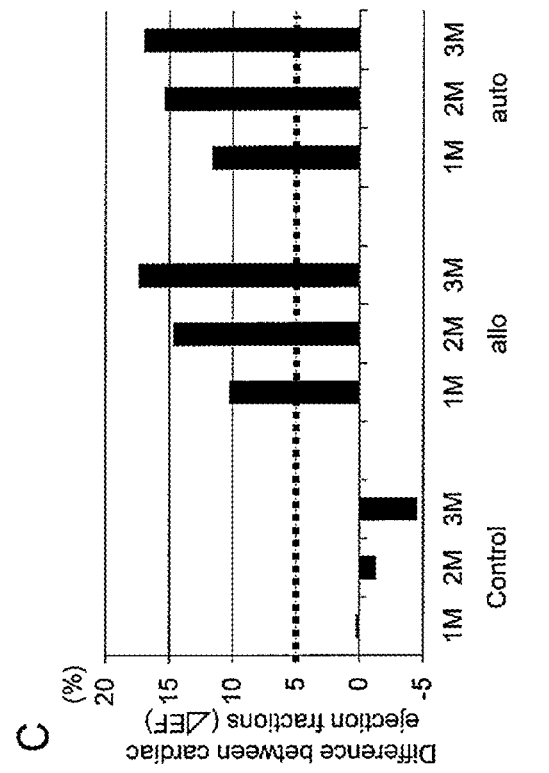
Figure 6:
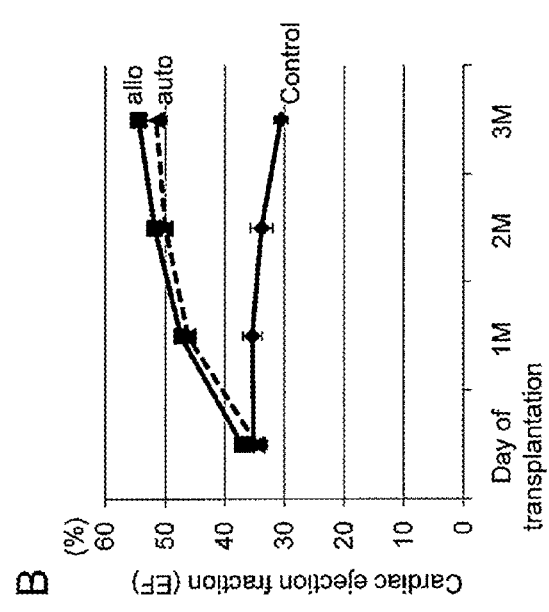

Test for Comparing Autologous Cells and Allogenic Cells in the Same Swine Species With the use of the same administration method and cardiac ejection fractions found by the same calculation method as that in Example 5, the effectiveness of a cell preparation (in FIG. 6: auto) containing myocardium-committed cells prepared with autologous cells, and that of a cell preparation (in FIG. 6: allo) containing myocardium-committed cells prepared with allogenic cells, in pigs with chronic myocardial infarction serving as severe heart failure model animals prepared in a manner similar to that in Example 5, were compared with that of a control (in which no cell preparation was administered). No immunosuppressive agent was administered to a group to which the cell preparation containing myocardium-committed cells prepared with allogenic cells was administered, so as to equalize the conditions with those in the case of autologous cells.

As a result, cardiac ejection fractions equivalent to or higher than that of autologous cells were confirmed for the groups to which the cell preparations had been administered, surprisingly without administration of any immunosuppressive agent and without any remarkable adverse reaction.

INDUSTRIAL APPLICABILITY

According to the present invention, a cell population containing myocardium-committed cells that differentiate into and survive as myocardial cells under a myocardial tissue environment is provided. The myocardium-committed cells exhibit higher expression levels of the markers of myocardial cells, intranuclear transcription factors including Nkx2.5, Islet-1 (also referred to as Is1-1), and GATA-4, myocardial constituting proteins including cardiac α-actin (α-CA), cardiac troponin I, myosin light chain (MLC), and myosin heavy chain (MHC), and, better ability to differentiate and survive, compared with conventional cardiac myoblasts cultured in the presence of DMSO or OP9 culture supernatant for induction of the differentiation thereof. Furthermore, the cell population of the present invention can be used effectively for treating heart failure such as ischemic cardiomyopathy by its infusion into the coronary artery, for example. Furthermore, the cell population or the cell preparation of the present invention prepared with allogenic cells are equivalent to or better than the same prepared with autologous cells, surprisingly without administration of any immunosuppressive agent and without any remarkable adverse reaction. When prepared with allogenic cells, the cell population or the cell preparation can be produced independent of cells from a patient to which the cell population or the cell preparation is administered. Hence, a cell preparation suitable for industrial production can be provided.

All publications, patents, and patent applications cited herein are incorporated herein by reference in their entirety.

The invention claimed is:

1. A method for producing a cell population comprising myocardium-committed cells, comprising a step of culturing adipose-tissue-derived multi-lineage/multi-potent progenitor cells for 1 to 5 days in the presence of a polyamine.

2. The method according to claim 1, further comprising collecting a cell population that comprises myocardium-committed cells in a percentage of at least 10% in all cells, from adipose-tissue-derived multi-lineage/multi-potent progenitor cells cultured in the presence of a polyamine.

3. The method according to claim 1, wherein the concentration of the polyamine in a medium ranges from 5 μM to 1 mM.

4. A method for producing a cell sheet, comprising the steps of:
    producing a cell population comprising myocardium-committed cells by the method of claim 1; and
    culturing the cell population to form a cell sheet.

* * * * *